US010406175B2

(12) United States Patent
Kurisawa et al.

(10) Patent No.: US 10,406,175 B2
(45) Date of Patent: *Sep. 10, 2019

(54) POLYMER-FLAVONOID CONJUGATE AND USES THEREOF

(71) Applicant: Agency for Science, Technology and Research, Singapore (SG)

(72) Inventors: Motoichi Kurisawa, Singapore (SG); Fan Lee, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 15/308,725

(22) PCT Filed: May 15, 2015

(86) PCT No.: PCT/SG2015/050117
§ 371 (c)(1),
(2) Date: Nov. 3, 2016

(87) PCT Pub. No.: WO2015/174934
PCT Pub. Date: Nov. 19, 2015

(65) Prior Publication Data
US 2017/0216446 A1     Aug. 3, 2017

(30) Foreign Application Priority Data

May 15, 2014 (SG) .......................... 10201402361X

(51) Int. Cl.
| | | |
|---|---|---|
| A61K 47/48 | (2006.01) | |
| A61K 31/353 | (2006.01) | |
| A61K 31/728 | (2006.01) | |
| C08B 37/00 | (2006.01) | |
| C08L 5/08 | (2006.01) | |
| C08B 37/08 | (2006.01) | |
| A61K 9/00 | (2006.01) | |
| A61K 47/61 | (2017.01) | |

(52) U.S. Cl.
CPC .......... *A61K 31/728* (2013.01); *A61K 9/0024* (2013.01); *A61K 31/353* (2013.01); *A61K 47/61* (2017.08); *C08B 37/0072* (2013.01); *C08L 5/08* (2013.01)

(58) Field of Classification Search
CPC .. A61K 47/48; A61K 47/4823; A61K 31/353; A61K 31/728
USPC .......................................................... 514/54
See application file for complete search history.

(56) References Cited

U.S. PATENT DOCUMENTS

| | | |
|---|---|---|
| 5,670,538 A | 9/1997 | Franchimont et al. |
| 6,428,817 B1 | 8/2002 | Collin |
| 7,858,080 B2 | 12/2010 | Chung et al. |
| 8,410,165 B2 | 4/2013 | Chung et al. |
| 2005/0220753 A1 | 10/2005 | Ji et al. |
| 2012/0196767 A1 | 8/2012 | Cooney et al. |
| 2016/0213787 A1 | 7/2016 | Kurisawa et al. |

FOREIGN PATENT DOCUMENTS

| | | | |
|---|---|---|---|
| CN | 101180319 A | 5/2008 | |
| EP | 0296740 A2 | 12/1988 | |
| JP | H07-238079 A | 9/1995 | |
| JP | H08-504213 A | 5/1996 | |
| JP | 2003-501381 A | 1/2003 | |
| JP | 2013-501781 A | 1/2013 | |
| JP | 2016-534136 A | 11/2016 | |
| WO | WO 00/74662 A2 * | 12/2000 | ............. A61K 31/00 |
| WO | WO-00/74662 A2 | 12/2000 | |
| WO | WO-2006/124000 A1 | 11/2006 | |
| WO | WO 2006/124000 A1 * | 11/2006 | ............. A61K 47/48 |
| WO | WO-2011/019323 A1 | 2/2011 | |
| WO | WO-2013/063086 A1 | 5/2013 | |
| WO | WO 2013/063086 A1 * | 5/2013 | ............. A61K 38/00 |
| WO | WO-2015/034436 A1 | 3/2015 | |
| WO | WO-2015/039989 A1 | 3/2015 | |

OTHER PUBLICATIONS

The Merck Manual, 1992, 16th Ed., pp. 1297-1300, 1305-07, 1338-1339.*
International Search Report for PCT/SG2015/050117, 5 pages (dated Aug. 24, 2015).
Lee, F. et al., Synthesis and bioactivity of a conjugate composed of green tea catechins and hyaluronic acid, Polymer Chemistry, 6(24): 4462-472 (2015).
Mori, T. et al., Covalent Binding of Tea Catechins to Protein Thiols: The Relationship between Stability and Electrophilic Reactivity, Biosci, Biotechnol. Biochem., 74(12): 2451-2456 (2010).
Written Opinion for PCT/SG2015/050117, 8 pages (dated Aug. 24, 2015).
Murray, M., Arthritis (Getting Well Naturally), English Translation, p. 76-77 (Sep. 1, 1994).
Lambert, J.D. et al., Anticancer and Anti-inflammatory Effects of Cysteine Metabolites of the Green Tea Polyphenol, (?)-Epigallocatechin-3-gallate, J. Agric. Food Chem., 58(18): 10016-10019 (2010).
Lambert, J.D. et al., N-Acetylcysteine enhances the lung cancer inhibitory effect of epigallocatechin-3-gallate and forms a new adduct, Free Radical Biology and Medicine, 44(6): 1069-1074 (2008).
Muzolf-Panek, M. et al., Role of Catechin Quinones in the Induction of EpRE-Mediated Gene Expression, Chem. Res. Toxicol., 21(12): 2352-2360 (2008).
Yasuda, H. and Arakawa, T., Deodorizing Mechanism of (-)-Epigallocatechin Gallate against Methyl Mercaptan, Biosci. Biotech. Bochem., 59(7):1232-1236 (1995).

* cited by examiner

*Primary Examiner* — Ganapathy Krishnan
(74) *Attorney, Agent, or Firm* — Choate, Hall & Stewart LLP

(57) ABSTRACT

There is provided a polymer-flavonoid conjugate, or a pharmaceutically acceptable salt thereof, uses thereof, and methods of making thereof. The disclosed polymer-flavonoid conjugates may be useful in the therapeutic and/or prophylactic treatment of a joint condition in a subject.

14 Claims, 7 Drawing Sheets

POLYMER-FLAVONOID CONJUGATE AND USES THEREOF

This patent application is a National Stage Entry of International Patent Application No. PCT/SG2015/050117, filed on May 15, 2015, which claims the benefit of priority of Singapore patent application No. 10201402361X, filed on May 15, 2014, the contents of each of which are hereby incorporated by reference in their entirety for all purposes herein.

TECHNICAL FIELD

The present invention generally relates to a polymer-flavonoid conjugate, uses and methods of making thereof. The polymer-flavonoid conjugates may be useful in the therapeutic and/or prophylactic treatment of a joint condition in a subject.

BACKGROUND

Osteoarthritis is a common degenerative joint disease that affects millions of people worldwide, particularly among the aging population. The symptoms of osteoarthritis include cartilage damage, subchondral bone sclerosis, osteophyte formation and synovial membrane inflammation. These symptoms worsen over time, causing pain and disability at the affected joints. Therefore, osteoarthritis significantly affects a patient's quality of life. The pathogenesis of osteoarthritis is complex and not fully understood. It is recognized that mechanical stress on the joint can lead to cartilage degeneration over time (wear and tear). Genetic factors contribute to osteoarthritis pathogenesis as the intrinsic quality of the cartilage and the anatomy of the joint can develop in ways that are more prone to damage. Inflammation is also involved in osteoarthritis development. Pro-inflammatory cytokines such as interleukin-1ß (IL-1ß) and tumor necrosis factor-α (TNF-α) are elevated in osteoarthritis cartilage, synovial fluid, synovial membrane and subchondral bone. These cytokines suppress the synthesis of cartilage extra-cellular matrix (ECM) and increase the production of matrix metalloproteinases (MMPs) which degrade type II collagen in the cartilage. Inflammation of the synovial membrane, or synovitis, leads to the infiltration of inflammatory cells which secrete more pro-inflammatory cytokines, aggravating the diseased condition by further increasing MMP production. Currently there is no cure for osteoarthritis. Existing treatments aim to alleviate pain and improve joint function through non-pharmacological and/or pharmacological modalities. If a patient does not benefit from a combination of non-pharmalogical and pharmalogical treatment, joint replacement surgery can be considered.

In recent years, flavonoids have attracted much attention because they have been recognized to have biological and pharmacological properties. However, the activity half-life of flavonoids is limited to a few hours inside the body. Therefore, despite the favorable properties of flavonoids, it is impractical to achieve a therapeutic level of this compound in the body by directly ingesting a large amount due to inherent volume constraint. That is, in order to obtain a therapeutic or pharmacological benefit from flavonoids through diet alone, it would be necessary to ingest an amount of food and beverage that is larger than is practical to consume.

In cases of flavonoids consumed via oral intake of foods and beverages, the flavonoids may play a role as antioxidants to protect the digestive tract from oxidative damage during digestion. However, flavonoids can be expected to remain only in the digestive tract and thus their beneficial physiological activities are not likely to be utilized in tissues. Moreover, their strong hydrophobicity as well as their tendency to form complexes with proteins makes parenteral delivery of these compounds difficult.

There is therefore a need to provide a treatment that overcomes, or at least ameliorates, one or more of the conditions described above.

SUMMARY

The present disclosure provides polymer-flavonoid conjugates, useful in the therapeutic and/or prophylactic treatment of a joint condition in a subject. The present disclosure further provides a process for forming said polymer-flavonoid conjugates.

According to a first aspect of the present disclosure, there is provided the use of a polymer-flavonoid conjugate, or a pharmaceutically acceptable salt thereof, in the manufacture of a medicament for the therapeutic and/or prophylactic treatment of a joint condition in a subject.

In a second aspect of the present disclosure, there is provided a polymer-flavonoid conjugate, or a pharmaceutically acceptable salt thereof, for use in the therapeutic and/or prophylactic treatment of a joint condition in a subject.

In a third aspect of the present disclosure, there is provided a method of treating or preventing a joint condition comprising administering a therapeutically effective amount of a polymer-flavonoid conjugate to a subject.

Advantageously, the disclosed polymer-flavonoid conjugates of the first to third aspects may be used in the treatment of osteoarthritis. The disclosed polymer-flavonoid conjugates of the first aspect may advantageously improve joint function and reduce pain.

Further advantageously, the disclosed polymer-flavonoid conjugates of the first to third aspects may restore a cartilage defect thereby repairing the cartilage.

Advantageously, the use of the disclosed polymer-flavonoid conjugates of the first to third aspects may potentially enhance the therapeutic outcome of the flavonoid. Further advantageously, the injection of the disclosed polymer-flavonoid conjugates of the first to third aspects may overcome the low bioavailability of flavonoids when administered orally. Further advantageously, the injection of the disclosed polymer-flavonoid conjugates of the first to third aspects may be at a low frequency.

In a fourth aspect of the present disclosure, there is provided a process for forming a polymer-flavonoid conjugate comprising the steps of:

(a) linking an amine-containing compound to one or more flavonoids to thereby form a flavonoid(s) bearing a free amine group; and (b) conjugating the product of (a) with a polymer via nucleophilic addition.

Advantageously, the disclosed process of the fourth aspect may allow for the conjugation of the polymer to the flavonoid through an efficient and cost-effective process.

DEFINITIONS

The following words and terms used herein shall have the meaning indicated:

As used herein, the term "joint condition" refers to a condition involving the modulation of tumor-necrosis factor-α (TNF-α), interleukin-6 (IL-6), matrix metalloproteinase-1 (MMP-1), matrix metalloproteinase-3 (MMP-3) and/ or matrix metalloproteinase-13 (MMP-13) expression(s). For example, the term "joint condition" refers to conditions associated with the joint and connective tissue of a subject and may include conditions such as arthritis, cartilage damage, joint pain, joint inflammation, systemic lupus erythematous, mixed connective tissue disease, subchondrol bone sclerosis, synovial membrane inflammation and osteophyte formation.

As used herein, the term "arthritis" refers to, for example, osteoarthritis, rheumatoid arthritis, gouty arthritis, juvenile arthritis, psoriatic arthritis, and ankylosing spondylitis.

As used herein, the term "joint pain" includes, for example, osteoarthritic joint pain, rheumatoid arthritic joint pain, inflammatory joint pain, acute joint pain and chronic joint pain.

As used herein, the term "joint inflammation" includes, for example, arthritic joint inflammation, osteoarthritic arthritic joint inflammation and rheumatoid arthritic joint inflammation.

As used herein, the term "cartilage damage" includes, for example, damage in an osteoarthritic joint or a rheumatoid arthritic joint.

As used herein, the term "cartilage repair" includes, for example, healing and regeneration of cartilage injuries, tears, deformities or defects, and prophylactic use in preventing damage to cartilaginous tissue. The cartilage injury may be in a joint.

As used herein, the term "amide" refers to a group of formula "—C(O)NRxRy," wherein Rx and Ry can be independently hydrogen, alkyl, aryl, cycloalkyl, cycloalkenyl or heterocycle.

As used herein, the term "amido" refers to a group of formula "—C(O)NRx-," wherein Rx can be hydrogen, alkyl, aryl, cycloalkyl, cycloalkenyl or heterocycle. The amido group may be attached to the parent molecular moiety through the carbonyl group or the amino group.

As used herein, the term "subject" refers to both human and non-human animals.

As used herein, the term "linker" refers to any chemical group that may link the polymer and the flavonoid and includes, for example, a molecule comprising one or more various groups of atoms including optionally substituted heteroalkyl, methylene groups (—CH$_2$—), straight alkylene groups, branched alkylene groups, aromatic groups, heteroaromatic groups, alicyclic groups, polyalkylene glycol groups (such as ethylene oxide groups; —O—CH$_2$—CH$_2$—), amide groups (—CONH—), amine groups (—NH—), amide groups (—NHC(O)— or —C(O)NH—), ether groups (—O—), carbamate grups, acetal groups, amido ester groups, alkenyl groups and combinations thereof. As used herein, the term "thiol linker" refers to a molecule including one or more thiol groups (—SH) joined covalently through one or more linking atoms. The thiol group(s) of the thiol linked can be joined through one or more various groups of atoms including methylene groups (—CH$_2$—), straight alkylene groups, branched alkylene groups, aromatic groups, heteroaromatic groups, alicyclic groups, polyalkylene glycol groups (such as ethylene oxide groups; —O—CH$_2$—CH$_2$—), amide groups (—CONH—), amine groups (—NH—), amide groups (—NHC(O)— or —C(O)NH—), ether groups (—O—), carbamate grups, acetal groups, amido ester groups, alkenyl groups and combinations thereof.

As used herein, the term "amine-containing compound" refers to a compound containing one or more amine groups (—NR$_2$, wherein R may independently be hydrogen, alkyl, aryl, cycloalkyl, cycloalkenyl or heterocycle).

As used herein, the term "heteroalkyl" refers to an alkyl moiety as defined above, having one or more carbon atoms, for example 1, 2, 3, 4, 5, 6, 7, 8, 9, 10 carbon atoms, replaced with one or more heteroatoms, which may be the same or different, where the point of attachment to the remainder of the molecule is through a carbon atom of the heteroalkyl radical, or the heteroatom. Suitable heteroatoms include O, S, and N. Non-limiting examples include ethers, thioethers, amines, hydroxymethyl, 3-hydroxypropyl, 1,2-dihydroxyethyl, 2-methoxyethyl, 2-aminoethyl, 2-dimethylaminoethyl, and the like. Heteroalkyl groups may be optionally substituted.

The term "optionally substituted" as used herein means the group to which this term refers may be unsubstituted, or may be substituted with one or more groups other than hydrogen provided that the indicated atom's normal valency is not exceeded, and that the substitution results in a stable compound. Such groups may be, for example, halogen, hydroxy, oxo, cyano, nitro, alkyl, alkoxy, haloalkyl, haloalkoxy, aryl4alkoxy, alkyithio, hydroxyalkyl, alkoxyalkyl, cycloalkyl, cycloalkylalkoxy, alkanoyl, alkoxycarbonyl, alkylsulfonyl, alkylsulfonyloxy, alkylsulfonylalkyl, arylsulfonyl, arylsulfonyloxy, arylsulfonylalkyl, alkylsulfonamido, alkylamido, alkylsulfonamidoalkyl, alkylamidoalkyl, arylsulfonamido, arylcarboxamido, arylsulfonamidoalkyl, arylcarboxamidoalkyl, aroyl, aroyl4alkyl, arylalkanoyl, acyl, aryl, arylalkyl, alkylaminoalkyl, a group R$^x$R$^y$N—, R$^x$OCO(CH$_2$)$_m$, R$^x$CON(R$^y$)(CH$_2$)$_m$, R$^x$R$^y$NCO(CH$_2$)$_m$, R$^x$R$^y$NSO$_2$(CH$_2$)$_m$ or R$^x$SO$_2$NR$^y$(CH$_2$)$_m$ (where each of R$^x$ and R$^y$ is independently selected from hydrogen or alkyl, or where appropriate R$^x$R$^y$ forms part of carbocyclic or heterocyclic ring and m is 0, 1, 2, 3 or 4), a group R$^x$R$^y$N(CH$_2$)$_p$— or R$^x$R$^y$N(CH$_2$)$_p$O— (wherein p is 1, 2, 3 or 4); wherein when the substituent is R$^x$R$^y$N(CH$_2$)$_p$— or R$^x$R$^y$N(CH$_2$)$_p$O, R$^x$ with at least one CH$_2$ of the (CH$_2$)$_p$ portion of the group may also form a carbocyclyl or heterocyclyl group and R$^y$ may be hydrogen, alkyl.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Exemplary, non-limiting embodiments of the disclosed polymer-flavonoid conjugates, uses and processes for making thereof will now be disclosed.

The present disclosure provides polymer-flavonoid conjugates, useful in the therapeutic and/or prophylactic treatment of a joint condition in a subject. The present disclosure further provides a process for forming said polymer-flavonoid conjugates.

In one aspect, there is provided the use of a polymer-flavonoid conjugate, or a pharmaceutically acceptable salt thereof, in the manufacture of a medicament for the therapeutic and/or prophylactic treatment of a joint condition in a subject.

In another aspect, there is provided a polymer-flavonoid conjugate, or a pharmaceutically acceptable salt thereof, for use in the therapeutic and/or prophylactic treatment of a joint condition in a subject.

In a further aspect, there is provided a method of treating or preventing a joint condition comprising administering a therapeutically effective amount of a polymer-flavonoid conjugate to a subject.

The joint condition may be selected from the group consisting of arthritis, cartilage damage, joint pain, joint inflammation, systemic lupus erythematous, mixed connective tissue disease, subchondrol bone sclerosis, synovial membrane inflammation and osteophyte formation.

The arthritis may be selected from the group consisting of osteoarthritis, rheumatoid arthritis, gouty arthritis, juvenile arthritis, psoriatic arthritis, and ankylosing spondylitis.

The therapeutic and/or prophylactic treatment of a joint condition may result in cartilage repair.

The disclosed polymer-flavonoid conjugates are useful in a method of treating or preventing a joint condition in a subject.

Polymer

The polymer may contain a free aldehyde or a group that can be converted to a free aldehyde in the presence of an acid, the polymer conjugated at the C6 and/or C8 position of the A ring of the flavonoid by attachment of the polymer via reaction of the free aldehyde group with the C6 and/or C8 position of the A ring of said flavonoid.

The polymer may be selected from the group consisting of polysaccharides, polynucleotides, polypeptides, synthetic polymers and mixtures thereof.

Said polysaccharide may be selected from the group consisting of hyaluronic acid (HA), dextran, cellulose, amylose, starch, gelatin, alginate, chitosan, carrageenan, cyclodextrin, dextran sulfate, Ficoll, gellan, guar gum, pectin, polysucrose, pullulan, scleroglucan, xanthan and xyloglucan.

The polysaccharide may be conjugated to at least one epigallocatechin gallate. The polysaccharide may be conjugated to one epigallocatechin gallate or to two epigallocatechin gallate.

The polysaccharide may be conjugated to at least one epigallocatechin gallate via a thiol linker.

The polysaccharide may be conjugated to at least one epigallocatechin gallate at the C6 and/or C8 position of the A ring of said epigallocatechin gallate.

The polynucleotide may be selected from the group consisting of aptamers, DNA, small interfering RNA (siRNA), microRNA, peptide nucleic acid (PNA) and small hairpin RNA (shRNA).

The polypeptide may be selected from the group consisting of proteins, antibodies, antibody fragments, aptides, peptides and poly(amino acid)s.

The synthetic polymer may comprise monomers selected from the group consisting of alkenes, ethers, carboxylic acids, imines, amides, amines, anhydrides, carbonates, esters, orthoesters and urethanes.

The synthetic polymer may be selected from the group consisting of poly(acrylamide), poly(allylamine), polyanhydrides, poly(β-amino ester), poly(butylene succinate), polycaprolactone, polycarbonate, polydioxanone, polyethylenimine, poly(glycerol), polyglycolic acid, poly(3-hydroxypropionic acid), poly(N-(2-hydroxypropyl) methacrylamide), polylactic acid, poly(lactic-co-glycolic acid), poly(acrylic acid), poly(methacrylic acid), poly(ortho esters), poly(2-oxazoline), poly(sebacic acid), poly(terephthalate-co-phosphate), poly(vinyl alcohol), poly(vinylpyrrolidone) and combinations thereof.

Flavonoid

The flavonoid may be any flavonoid from the general class of molecules derived from a core phenylbenzyl pyrone structure. A simplified depiction of the A, B, and C rings of a flavonoid is shown below:

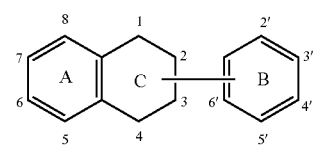

By the term "flavonoid", it is intended to include flavones, isoflavones, flavonols, flavanones, flavan-3-ols, catechins, anthocyanidins an chalcones. In a particular embodiment the flavonoid is a catechin or a catechin-based flavonoid. A catechin, or a catechin-based flavonoid is any flavonoid that belongs to the class generally known as catechins (or flavan-3-ol derivatives), and includes catechin and catechin derivatives, including epicatechin, epigallocatechin, catechin, epicatechin gallate and epigallocatechin gallate, and including all possible stereoisomers of catechins or catechin-based flavonoids. In particular embodiments, the catechin-based flavonoid is (+)-catechin or (−)-epigallocatechin gallate. The flavonoid of the disclosed polymer-flavonoid conjugates may be selected from the group consisting of flavones, isoflavones, flavans, proanthocyanidins and anthocyanidins.

The flavonoid may be selected from the group consisting of (−)-epicatechin, (+)-epicatechin, (−)-catechin, (+)-catechin, epicatechin gallate, epigallocatechin, epigallocatechin gallate, Fisetinidol, Gallocatechin, Gallocatechin gallate, Mesquitol and Robinetinidol, ellagitannin, gallotannin, oolongtheanin, phlorotannin, tannin, theacitrin, theadibenzotropolone, theaflavin, theanaphthoquinone, thearubigins, theasinensin and mixtures thereof.

The flavonoid may be a single monomeric unit of a flavonoid or it may be a dimer, or an oligomer of one or more flavonoids. The oligomer of the flavonoid may be of 2 or more monomeric units linked together.

In one embodiment, the flavonoid may be epigallocatechin gallate (EGCG):

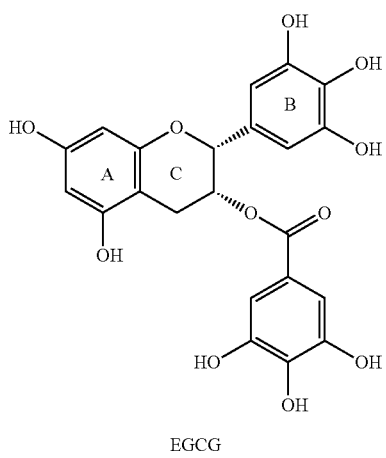

EGCG

Polymer-Flavonoid Conjugates

At least one flavonoid may be bonded to said polymer. At least two flavonoids may be bonded to said polymer.

The polymer may be bonded to said flavonoid via a linker. The linker may be any chemical group that may link the polymer and the flavonoid. The linker may be selected from the group comprising a thiol, amide, thioether, imine, amine, azo and/or 1,2,3-triazole group. The linker may be present between any part of the polymer and any part of the flavonoid. The linker may be present between a terminus of the polymer and any part of the flavonoid.

The polymer of the polymer-flavonoid conjugate may have one or more flavonoids conjugated to the polymer. The flavonoid may be selected from the group consisting of a monomeric flavonoid or a dimeric flavonoid. A monomeric flavonoid may comprise one flavonoid molecule. A dimeric flavonoid may comprise two flavonoid molecules linked together by a linker. One of the flavonoid molecules of the dimeric flavonoid may be linked to the polymer. Both of the flavonoid molecules of the dimeric flavonoid may be independently linked to the polymer. When one flavonoid is present in said conjugate, the flavonoid may be bonded to said polymer via the B ring. When two flavonoids are present in said conjugate, the flavonoid may be bonded to said polymer via the A ring.

The polymer of the polymer-flavonoid conjugates may be conjugated to the flavonoid at the A ring of said flavonoid. The polymer of the polymer-flavonoid conjugates may be conjugated to the flavonoid at the C6 and/or C8 position of the A ring of said flavonoid.

The free aldehyde group on the polymer may allow for the conjugation of the polymer in a controlled manner to either the C6 or the C8 position of the A ring or both, of the flavonoid structure, thus preventing disruption of the flavonoid structure, particularly the B and C rings of the flavonoid, and thus preserving the beneficial biological and pharmacological properties of the flavonoid.

The polymer of the polymer-flavonoid conjugates may be conjugated to the flavonoid at the B ring of said flavonoid. The polymer of the polymer-flavonoid conjugates may be conjugated to the flavonoid at the C2 and/or C6 position of the B ring of said flavonoid.

The polymer may be conjugated to the flavonoid via a thiol linker.

In another embodiment, the polymer of the polymer-flavonoid conjugate is conjugated to the flavonoid via a thiol linker. The thiol linker may further comprise a moiety bound to the polymer, wherein said moiety is selected from the group consisting of an amide, an amine, an alkyl, an alkenyl, an aryl, an ester, a carbonate, an ether, an amido, an amido ester, a carbamate and an acetal group. The alkyl group may have 1, 2, 3, 4, 5, 6, 7, 8, 9, or 10 carbon atoms. The alkenyl group may have 1, 2, 3, 4, 5, 6, 7, 8, 9, or 10 carbon atoms. The aryl group may have 6, 7, 8, 9, or 10 carbon atoms.

The thiol linker may further comprise a moiety bound to the polymer, wherein said moiety is selected from the group consisting of an amide, an amine, an alkyl, an alkenyl, an aryl, an ester, a carbonate, an ether, an amido, an amido ester, a carbamate and an acetal group.

The disclosed polymer-flavonoid conjugate may be of Formula 1:

Formula 1

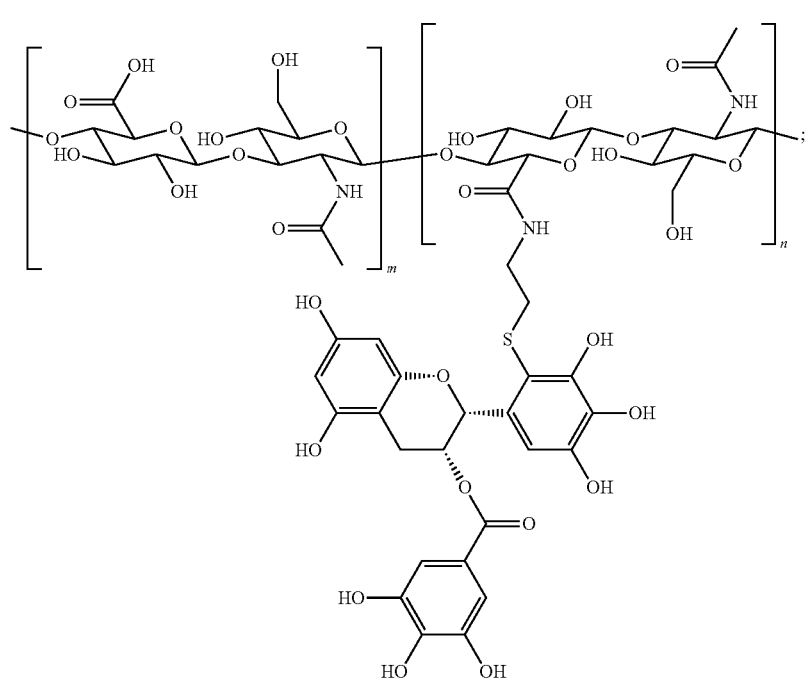

wherein:
each n is independently an integer from 0 to 50,000 inclusive; and each m is independently an integer from 0 to 50,000 inclusive, wherein at least one of n or m is not 0.

The polymer-flavonoid conjugate may be of Formula 2:

wherein:
each n is independently an integer from 0 to 50,000 inclusive; and each m is independently an integer from 0 to 50,000 inclusive, wherein at least one of n or m is not 0.

Formula 2

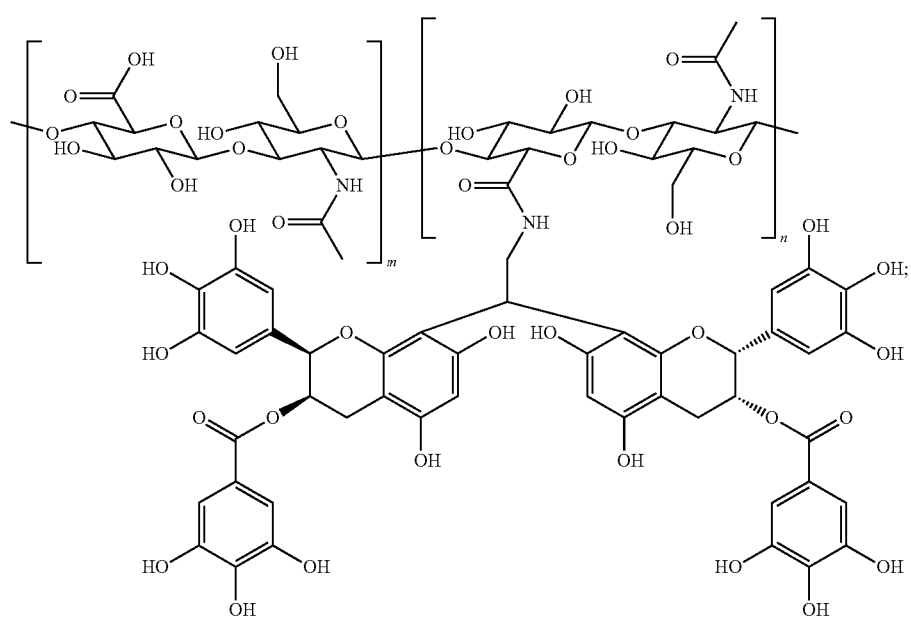

The disclosed polymer-flavonoid conjugate may have a degree of conjugation from 0.1 to 100%, or 0.1 to 90%, or 0.1 to 80%, or 0.1 to 70%, or 0.1 to 60%, or 0.1 to 50%, or 0.1 to 40%, or 0.1 to 30%, or 0.1 to 20%, or 0.1 to 10%, or 10 to 100%, or 20 to 100%, or 30 to 100%, or 40 to 100%, or 50 to 100%, or 60 to 100%, or 70 to 100%, or 80 to 100%, or 90 to 100%, or 0.1%, 10%, 20%, 30%, 40%, 50%, 60%, 70%, 80%, 90%, or 100%.

The disclosed polymer-flavonoid conjugates are useful in the treatment of joint conditions, for example, in the treatment of osteoarthritis.

It was surprisingly found that cells were more viable in the presence of a polymer-flavonoid conjugate compared to a flavonoid alone, suggesting that conjugation of a flavonoid to a polymer reduced the toxicity of the flavonoid. Stimulation of osteoarthritis chondrocytes with IL-1ß increased the mRNA and protein expressions of inflammatory cytokines and MMPs. It was shown that while the flavonoid may effectively inhibit IL-1ß-induced gene and protein expressions, polymer alone or polymer-flavonoid conjugates fails to downregulate IL-6 and TNF-α expressions. However, polymer-flavonoid conjugates were surprisingly found to be more effective than polymer alone in downregulating MMP-1, MMP-3 and MMP-13 expressions, especially at the protein level. Inhibition of MMP protein expressions by polymer-flavonoid conjugates were shown to be concentration-dependent. It is advantageously shown that polymer-flavonoid conjugates may be successful therapeutic agents for the treatment of osteoarthritis.

Process for Forming Polymer-Flavonoid Conjugates

There is also provided a process for forming a polymer-flavonoid conjugate comprising the steps of:
(a) linking an amine-containing compound to one or more flavonoids to thereby form a flavonoid(s) bearing a free amine group; and
(b) conjugating the product of (a) with a polymer via nucleophilic addition.

Step (a) may comprise linking an amine-containing compound to two flavonoids to thereby form an amine-containing-bridged flavonoid dimer.

Step (b) may be conducted in the presence of a coupling agent.

The coupling agent may be selected from the group consisting of 1-ethyl-3-(3-dimethylaminopropyl)-carbodiimide hydrochloride (EDC.HCl), hydrochloridel-ethyl-3-(3-dimethyl dicyclohexylcarbodiimide (DCC), diisopropylcarbodiimide (DIC), carbonyldiimidazole, dimethyl adipimidate, N-hydroxysuccinimide, p-nitrophenyl chloroformate and 1-(p-toluenesulfonyl)imidazole.

The conjugate may be synthesized using acid catalysis of a condensation of the aldehyde group of the polymer with the catechin-based flavonoid, or using acid to convert a functional group on the polymer to a free aldehyde prior to condensation of the aldehyde group with the catechin-based flavonoid.

To conjugate the polymer and the flavonoid, the polymer and the flavonoid may be separately dissolved in a suitable solvent. The polymer with the free aldehyde is added, for example by dropwise addition, to the solution containing the flavonoid, in the presence of an acid. The reaction is allowed to go to completion. Following the conjugation reaction, excess unreacted polymer or flavonoid can be removed from the conjugate composition, for example by dialysis or by molecular sieving.

The ratio of flavonoid to polymer may be varied, so that there is only one polymer moiety attached to the flavonoid portion of the polymer, or so that there is a flavonoid portion attached at more than one position on the polymer, or so that the flavonoid portion has two polymer portions attached, one at either of the C6 and C8 positions of the flavonoid.

The ratio of polymer to flavonoid in the final composition can be controlled through the ratio of starting reagents. For example, when the molar ratio of polymer moiety to flavonoid moiety is about 1, a single polymer moiety will be attached to a single flavonoid moiety (either monomeric or oligomeric may be used). However, at higher concentrations of polymer, for example at a 10:1 molar ratio of polymer to flavonoid, a composition having a tri-block structure of polymer-flavonoid-polymer may be obtained.

Delivery Vehicles

Conjugation of the polymer also allows for the incorporation of flavonoids into various compositions or vehicles. By selection of the particular polymer containing a free aldehyde group based on the physical properties of the polymer, it is possible to incorporate flavonoids into a variety of different vehicle types, allowing for the delivery of high concentrations of flavonoids in different contexts to various targeted areas of the body.

Thus, the presently disclosed polymer-flavonoid conjugates may be formed into a delivery vehicle, depending on the nature of the polymer portion of the conjugate. The delivery vehicle may be used to deliver the flavonoid to a body, including a particular targeted site in a body, depending on the nature of the delivery vehicle. Optionally, a bioactive agent may be included in the delivery vehicle, which may then be simultaneously delivered to the site in the body. Thus, there is provided a delivery vehicle comprising a composition that comprises comprising a flavonoid conjugated to a polymer through a free aldehyde group on the polymer, the delivery vehicle optionally further comprising a bioactive agent. The bioactive agent may be any agent that has a biological, pharmacological or therapeutic effect in a body, and includes a protein, a nucleic acid, a small molecule or a drug. A bioactive agent that is a protein may be a peptide, an antibody, a hormone, an enzyme, a growth factor, or a cytokine. A bioactive agent that is a nucleic acid may be single stranded or double stranded DNA or RNA, a short hairpin RNA, an siRNA, or may comprise a gene encoding a therapeutic product. In addition, included in the scope of bioactive agent are antibiotics, chemotherapeutic agents and antihypertensive agents. In one particular embodiment, the delivery vehicle is a micellar nanocomplex, which is suitable for parenteral delivery of flavonoid, and optionally bioactive agents to a particular site within a body. The polymer is chosen to have properties that allow it to assemble with the flavonoid portion of the composition, protecting the flavonoid from the solution environment. If a suitable solvent is chosen in which the polymer portion of the conjugate is soluble and is more soluble than the flavonoid, the conjugate may self assemble, excluding the solution from the flavonoid core, thus allowing for assembly of micellar complexes.

The concentration of the bioactive agent is chosen depending on the total amount of bioactive agent that is to be delivered to a particular site in a body, and on the amount of bioactive agent that can be included in the micellar nanocomplex without destabilizing the micellar structure. In certain embodiments, up to 50%, or up to 40%, w/w of the micellar complex may comprise the bioactive agent.

In another particular embodiment, the delivery vehicle is a hydrogel, which can be used as a wound or burn dressing, for sustained release delivery of a bioactive agent, as a support for tissue regeneration, for treatment of arthritis, or for cosmetic applications such as a facial mask.

The polymer may have good swellability characteristics and appropriate groups available for cross-linking of the polymer moieties, as well as non-toxic and biocompatible, and in some embodiments, biodegradable.

In a particular embodiment of the hydrogel, the polymer is an aldehyde derivatized hyaluronic acid, or a derivative of hyaluronic acid such as hyaluronic acid aminoacetylaldehyde dialkylacetal conjugate, or a tyramine derivative of the aldehyde derivatized hyaluronic acid or hyaluronic acid aminoacetylaldehyde dialkylacetal conjugate. Examples of a aminoacetylaldehyde dialkylacetal conjugate include, for example, aminoacetylaldehyde dimethylacetal, aminoacetylaldehyde diethylacetal conjugate, aminoacetylaldehyde dipropylacetal and aminoacetylaldehyde dibutylacetal.

Conjugates comprising a hyaluronic acid-flavonoid can be readily cross-linked to form a hydrogel, without disruption of the biological or pharmacological properties of the flavonoid. Such hydrogels may also optionally comprise a bioactive agent as described above, for release of the bioactive agent at the site where the hydrogel is applied.

The hyaluronic acid-flavonoid conjugate may be synthesized by reacting the hyaluronic acid with the flavonoid under acidic conditions, for example at pH of about 1. The conjugated polymer-flavonoid is then purified, for example by dialysis, and then mixed with bioactive agent and a cross-linking agent, such as hydrogen peroxide. A cross-linking catalyst is added, for example horseradish peroxidase, and the hydrogel may then be quickly poured in to a mold to form a desired shape before the cross-linking reaction is completed. For example, the hydrogel may be formed into a slab suitable for application as a wound dressing.

The components of the hydrogel may also be injected and reacted to form the hydrogel in vivo, for example by injecting an uncrosslinked conjugate, optionally with a bioactive agent, together with a cross-linking agent, such as hydrogen peroxide and a cross-linking catalyst, for example, horseradish peroxidase. Such a hydrogel is useful for drug delivery to a specific site in a body, or for tissue engineering.

Since hyaluronic acid has multiple sites that may react with the flavonoid during the conjugation reaction, by varying the concentration of the flavonoid in the starting reaction, it is possible to vary the degree of conjugation between the hyaluronic acid polymer and the flavonoid. For example, the ratio of reactants may be adjusted so that the resulting conjugate has from about 1% to about 10% of the sites on the polymer conjugated with the flavonoid. Alternatively, additional hyaluronic acid that has not been conjugated can be added to the mixture prior to cross-linking of the hydrogel so that some of the polymer molecules in the hydrogel will not be conjugated to the flavonoid.

The above described compositions and delivery vehicles are well-suited for controlled and targeted delivery of flavonoids to particular sites within the body. The flavonoids can provide antibacterial, antineoplastic, antithrombotic, vasodilatory, antioxidant, anti-mutagenic, anti-carcinogenic, hypercholesterolemic, antiviral and anti-inflammatory activity at the targeted site. Thus, the above conjugates and delivery vehicles are useful for a variety of treatment applications. In addition, the delivery vehicles can include an additional bioactive agent, making the delivery vehicles useful in the treatment of a wide range of disorders or diseases. For example, immunoregulatory peptides and proteins including cytokines and growth factors have emerged as an important class of drugs for the treatment of cancer, myelodepresssion and infectious disease.

Thus, there is presently provided a method of delivering a flavonoid to a subject comprising administering a conjugate of a polymer containing a free aldehyde and a flavonoid, having the polymer conjugated at the C6 and/or the C8 position of the A ring of the flavonoid is also contemplated, as described above. In certain embodiments, the conjugate is formed into a delivery vehicle, such as a micellar nanocomplex or a hydrogel, as described above.

The conjugate may be administered using known methods, which will depend on the form of the conjugate. Non-oral routes are preferred, particularly if a bioactive agent is being administered simultaneously in the same form with the conjugate. If the conjugate is formulated as a solution, or in the form of micellar nanoparticles, the conjugate may be delivered parenterally, including intravenously, intramuscularly, or by direct injection into a targeted tissue or organ. If the conjugate is formulated as a hydrogel, the conjugate may be applied topically or by surgical insertion at a wound site.

Administration

The conjugate may be administered in combination with a bioactive agent, particularly where the conjugate is formulated as a delivery vehicle as described above.

When administered to a patient, the conjugate is administered in an amount effective and at the dosages and for sufficient time period to achieve a desired result. For example, the conjugate may be administered in quantities and dosages necessary to deliver a flavonoid which may function to alleviate, improve, mitigate, ameliorate, stabilize, prevent the spread of, slow or delay the progression of or cure an infection, disease or disorder, or to inhibit, reduce or impair the activity of a disease-related enzyme. A disease-related enzyme is an enzyme involved in a metabolic or biochemical pathway, which when the pathway is interrupted, or when regulatory control of the enzyme or pathway is interrupted or inhibited, the activity of the enzyme is involved in the onset or progression of a disease or disorder.

The effective amount of conjugate to be administered to a subject can vary depending on many factors such as the pharmacodynamic properties of the conjugate, including the polymer moiety and the catechin-based flavonoid moiety, the mode of administration, the age, health and weight of the subject, the nature and extent of the disorder or disease state, the frequency of the treatment and the type of concurrent treatment, if any, and the concentration and form of the conjugate.

One of skill in the art can determine the appropriate amount based on the above factors. The conjugate may be administered initially in a suitable amount that may be adjusted as required, depending on the clinical response of the subject. The effective amount of conjugate can be determined empirically and depends on the maximal amount of the conjugate that can be administered safely. However, the amount of conjugate administered should be the minimal amount that produces the desired result.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 2 shows a graph depicting the effects of EGCG, HA (90 kDa) and HA-EGCGI conjugates on IL-1ß-induced IL-6 and TNF-α expressions in OA chondrocytes. Cells were treated with EGCG (10 µM), HA (0.1 and 1.1 mg/ml) or HA-EGCG1 conjugate (0.1 and 1.1 mg/ml containing 10 and 100 µM of EGCG, respectively) in the presence of IL-1ß (5 ng/ml). Gene expressions (top row) were analyzed using RT-PCR and protein concentrations (bottom row) in the culture medium were measured by ELISA.

Figure 3:
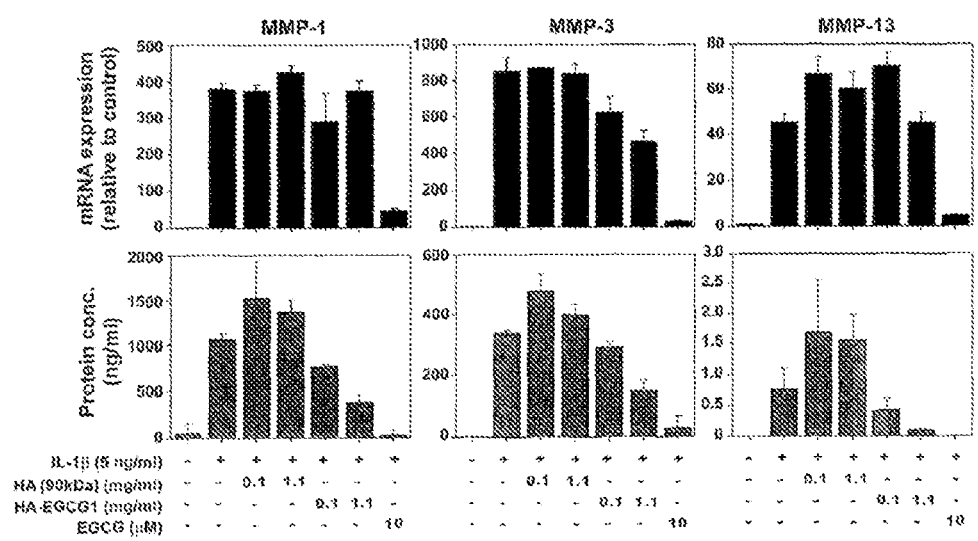

FIG. 3 shows a graph depicting the effects of EGCG, HA (90 kDa) and HA-EGCG1 conjugates on IL-Iß-induced MMP-1, MMP-3 and MMP-13 expressions in osteoarthritis chondrocytes. Cells were treated with EGCG (10 µM), HA (0.1 and 1.1 mg/ml) or HA-EGCG1 conjugate (0.1 and 1.1 mg/ml containing 10 and 100 µM of EGCG, respectively) in the presence of IL-1ß (5 ng/ml). Gene expressions (top row) were analyzed using RT-PCR and protein concentrations (bottom row) in the culture medium were measured by ELISA.

Figure 4:
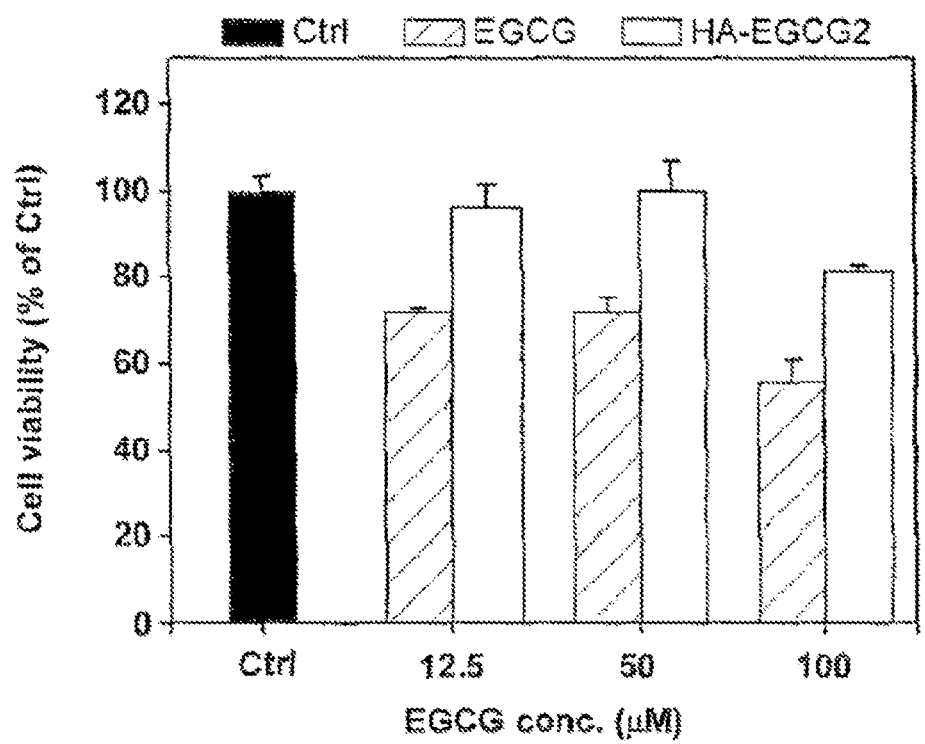

FIG. 4 shows a graph depicting cell viability of EGCG and HA-EGCG2 conjugates using human rheumatoid arthritis fibroblast-like synoviocytes (HA-EGCG2 concentrations: 0.2, 0.9 and 1.8 mg/ml which contained 12.5, 50 and 100) 1M of EGCG, respectively).

Figure 5:
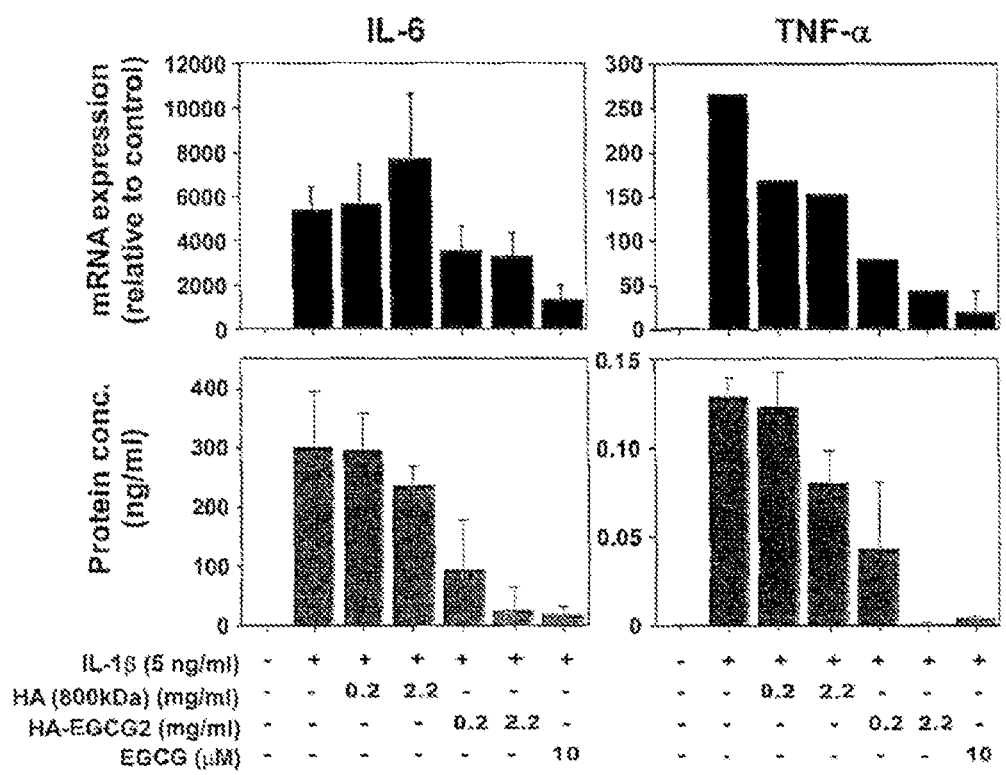

FIG. 5 shows a graph depicting the effect of EGCG, HA (800 kDa) and HA-EGCG2 conjugates on IL-1ß-induced IL-6 and TNF-α expressions in OA chondrocytes. Cells were treated with EGCG (10 µM), HA (0.2 and 2.2 mg/ml) or HA-EGCG1 conjugate (0.2 and 2.2 mg/ml containing 10 and 100 µM of EGCG, respectively) in the presence of IL-1ß (5 ng/ml). Gene expressions (top row) were analyzed using RT-PCR and protein concentrations (bottom row) in the culture medium were measured by ELISA.

Figure 6:
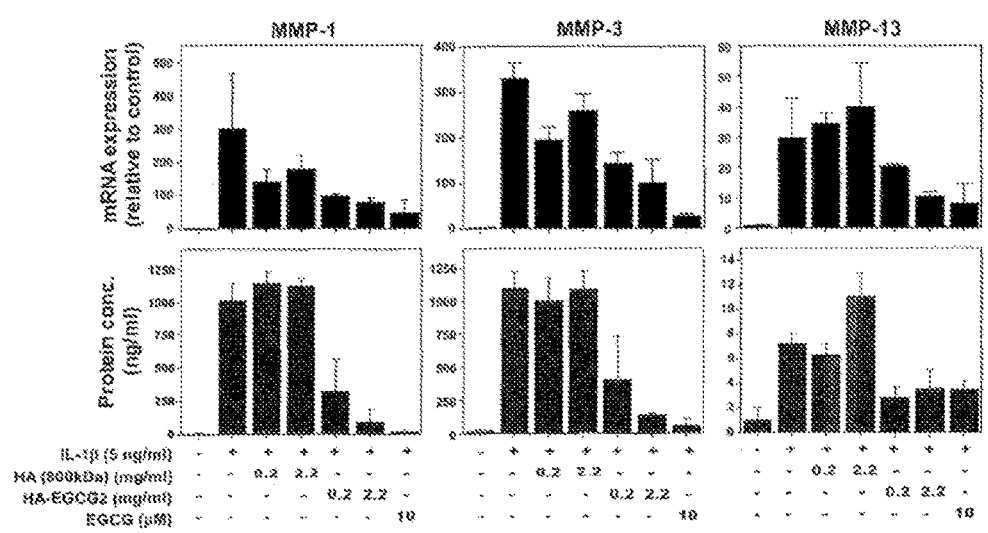

FIG. 6 shows a graph depicting the effects of EGCG, HA (800 kDa) and HA-EGCG2 conjugates on IL-1ß-induced MMP-1, MMP-3 and MMP-13 expressions in OA chondrocytes. Cells were treated with EGCG (10 µM), HA (0.2 and 2.2 mg/ml) or HA-EGCG1 conjugate (0.2 and 2.2 mg/ml containing 10 and 100 µM of EGCG, respectively) in the presence of IL-1ß (5 ng/ml). Gene expressions (top row) were analyzed using RT-PCR and protein concentrations (bottom row) in the culture medium were measured by ELISA.

Figure 7:
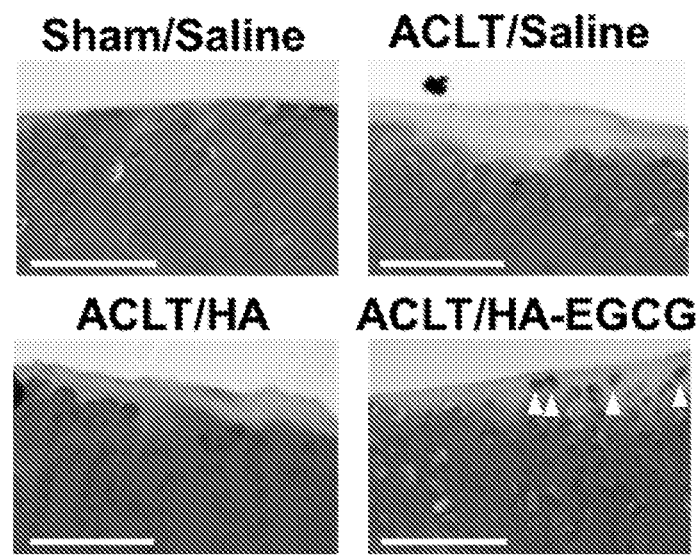

FIG. 7 is a rat anterior cruciate ligament transection (ACLT) model of osteoarthritis which shows the effects of intra-articular injection of saline, HA (800 kDa) and HA-EGCG2 conjugates on the structure of medial tibial condyle.

EXAMPLES

Non-limiting examples of the invention and a comparative example will be further described in greater detail by reference to specific Examples, which should not be construed as in any way limiting the scope of the invention.

Materials

Hyaluronic Acid (HA) (90 and 800 kDa) was obtained from JNC Corp (Tokyo, Japan). Tris(2-carboxyethyl)phosphine hydrochloride, cysteamine hydrochloride, methanesulfonic acid (MSA), 2,2-diethoxyethylamine (DA), N-hydroxysuccinimide (NHS), 1-ethyl-3-(3-dimethylaminopropyl)-carbodiimide hydrochloride (EDC), dimethyl sulfoxide (DMSO) and sodium chloride (NaCl) were obtained from Sigma (Singapore). 2-(N-Morpholino) ethanesulfonic acid (MES) was purchased from Merck (Singapore). Dulbecco's Modified Eagle Medium: Nutrient Mixture F-12 was supplied by media preparation facility in Biopolis (Singapore).

Example 1: Synthesis of HA-EGCG1 Conjugates

Thiolated HA derivatives were synthesized by modifying carboxyl groups in HA backbone with thiol groups. Typically, 1 g of HA (90 kDa, 2.5 mmol —COOH) was dissolved in 100 mL of distilled water under nitrogen atmosphere. To this solution, cysteamine hydrochloride (136 mg, 1.2 mmol) was added. EDC.HCl (485 mg, 2.5 mmol) and NHS (290 mg, 2.5 mmol) were then added to initiate the conjugation reaction. As the reaction proceeded, the pH of the mixture was maintained at 4.7 with 1M NaOH. The reaction mixture was stirred overnight at 25° C. and then the pH was brought to 7.0. The solution was transferred to dialysis tubes with a molecular weight cut-off of 3,500 Da. The purified solution was lyophilized to obtain HA-cysteamine conjugate (0.84 g). The degree of substitution (DS) is defined as the number of substituents per 100 repeating disaccharide units in HA. DS was determined to be 7 by Ellman's assay. The dried HA-cysteamine conjugate (0.5 g, 87.5 µmol —SH) was dissolved in 24.5 mL of 0.1 M phosphate buffer (pH 8.0). To this solution, 1.5 mL of 0.5 M TCEP solution was added. EGCG (3.45 mmol, 1.567 g) was dissolved in a premixed solvent (25 mL of 0.1 M phosphate buffer (pH 8.0), 5 mL of DMSO, and 1 mL of 100 mM sodium pyruvate). This solution was then added to a stirred solution of HA-cysteamine conjugate. The reaction mixture was incubated for 3 hours at 25° C. while stirring. Then, 5 mL of DMSO was added and stirred overnight at 25° C. The pH of the mixture was brought to 5 by adding 1% acetic acid before transferring the solution to dialysis tubes with a molecular weight cut-off of 3,500 Da. The tubes were dialyzed against distilled water for 3 days under nitrogen atmosphere. The purified solution was lyophilized to obtain EGCG-grafted HA (0.48 g). DS was determined by measuring the absorbance of EGCG at 273 nm. DS was 3.72. The structure of the product was confirmed by 1H NMR spectroscopy. 1H NMR (D$_2$O): δ 2.0 (s, —C═OCH$_3$ from HA), 3.3-4.0 (m, protons of HA), 4.51 and 4.54 (d, HA anomeric proton), 5.60-5.85 (s, H-2 and H-3 of C ring), 6.7 (s, H-6' of B ring), 6.98 (s, H-2" and H-6" of D ring).

Example 2: Synthesis of HA-EGCG2 Conjugates

First, ethylamine-bridged EGCG dimers were synthesized. To 1.2 ml of cold MSA:THF (1:5, v/v) mixture, 145 µl of DA (1 mmol) was added. The resulting mixture was transferred dropwise to EGCG (2.29 g, 5 mmol), which was dissolved in 3.8 ml of THF and 1.7 µl of MSA. The reaction was allowed to proceed overnight in the dark at room temperature. Next day, the solvent was removed by evaporation and further dried under vacuum overnight. The dried products were dissolved in 10 ml of H$_2$O. Unreacted EGCG was removed by extraction with 10 ml of ethyl acetate using a separation funnel. The extraction procedure was repeated until no free EGCG was detected in the aqueous phase using a Waters Acuity UPLC-MS. The ethylamine-bridged EGCG dimers were conjugated to HA by a carbodiimide/active ester-mediated coupling reaction. HA (800 kDA, 250 mg, 0.62 mmol) was dissolved by stirring in 20.2 ml of 0.4 M MES buffer (pH 5.2) with 2.5 ml of DMF. Next, NHS (89 mg, 0.78 mmol) and ethylamine-bridged dimers (0.205 mmol in 2.33 ml of H$_2$O) were added. Then, EDC-HCl (150 mg, 0.78 mmol) was added and the pH of the reaction was adjusted to 4.7. The reaction mixture was purged vigorously with N$_2$ for 10 minutes and then incubated in the dark overnight under N2 at room temperature. HA-EGCG2 conjugates were purified by precipitation. Briefly, 125 ml of H$_2$O and 16.7 ml of 5 M NaCl solution were added to the reaction mixture and the pH was lowered to 3 with 10 M HCl solution. Then 310 ml of ethanol was added while stirring. The precipitates were collected by centrifugation (6000 rcf, 5 min). After decanting the supernatant, the precipitates were re-dissolved in 250 ml of water. After adding 33 ml of 5 M NaCl solution and the pH adjusted to 3, 620 ml of ethanol was added. The precipitates were collected by centrifugation and re-dissolved in 500 ml of $H_2O$. After adding 67 ml of 5 M NaCl solution and lowering the pH to 3, 1.24 L of ethanol was added. The precipitates were again collected by centrifugation and re-dissolved in 300 ml of $H_2O$. The conjugates were then dialyzed (Spectra/Por 7, MWCO=3500 Da) against $H_2O$ in $N_2$ overnight. The purified HA-EGCG2 conjugates were lyophilized. The yield was 185 mg (74%). To determine the degree of substitution (number of EGCG dimers conjugated for every 100 disaccharide units), the conjugates were dissolved at 0.5 mg/ml in water and the absorbance spectrum was recorded. The amount of EGCG contained in the conjugate was determined by absorbance at 273 nm and the DS was 1.

Example 3: Culture of Human Osteoarthritis Chondrocytes

Cryopreserved human osteoarthritis chondrocytes (passage 1) were obtained from Cell Applications, INC. (USA). The cells were thawed and cultured in T75 cell culture flasks using complete growth medium (DMEM/F12 medium supplemented with 10% FBS and 1% penicillin/streptomycin). The cells were maintained at 37° C. and 5% $CO_2$ atmosphere. Growth medium was replaced every 2-3 days and the cells were subcultured at 80% confluency. Only cells at passage 2 and 3 were used in this study. After expansion, the cells were re-differentiated in alginate beads according to previously established protocol with some modifications. Briefly, cells were trypsinized, pelleted and resuspended in 1.2% (w/v) sodium alginate in 0.15 M NaCl. The cell suspension was dispensed through a 210 needle dropwise into gelation solution (102 mM $CaCl_2$, 10 mM HEPES and 0.0005% Tween 20, pH 7.4). Approximately 15 alginate beads were dispensed in 5 ml of gelation solution in a 6-wellplate. After gelation for 10 min, the gelation solution was removed and the alginate beads were washed twice with 5 ml of 0.15 M NaCl. Complete growth medium (5 ml) was then added and the cells were re-differentiated for 8 days in the alginate beads. Medium was changed every 2-3 days. After 8 days, the alginate beads were solubilized in dissolution solution (55 mM EDTA and 10 mM HEPES, pH 7.4). The recovered cells were pelleted and resuspended in complete growth medium at $0.5 \times 10^6$ cells/ml. For cell viability assay, 100 μl of cell suspension was added per well of a 96-wellplate. For gene and protein expression study, 200 μl of cell suspension was added per well of 48-wellplate. After overnight incubation, the cells were serum-starved for 12 hours prior to stimulation with IL-1ß and/or treatment with HA-EGCG conjugates.

Example 4: Cell Viability Assay

After serum starvation, the spent medium was removed and EGCG, HA, HA-EGCG1 or HA-EGCG2 conjugates were added in 100 μl of serum-free medium. Cells without drugs served as controls. After 24 hours incubation, cell viability was assessed by alamarBlue® according to manufacturer's instruction. Human OA chondrocytes were used to determine cell viability in the presence of HA-EGCG1 conjugates. Human rheumatoid arthritis fibroblast-like synoviocytes were used to determine cell viability in the presence of HA-EGCG2 conjugates. The synoviocytes were cultured in RMPI medium supplemented with 10% FBS and 1% penicillin/streptomycin. The cells were seeded and serum starved following the same protocol as osteoarthritis chondrocytes before performing cell viability assay.

Figure 1:
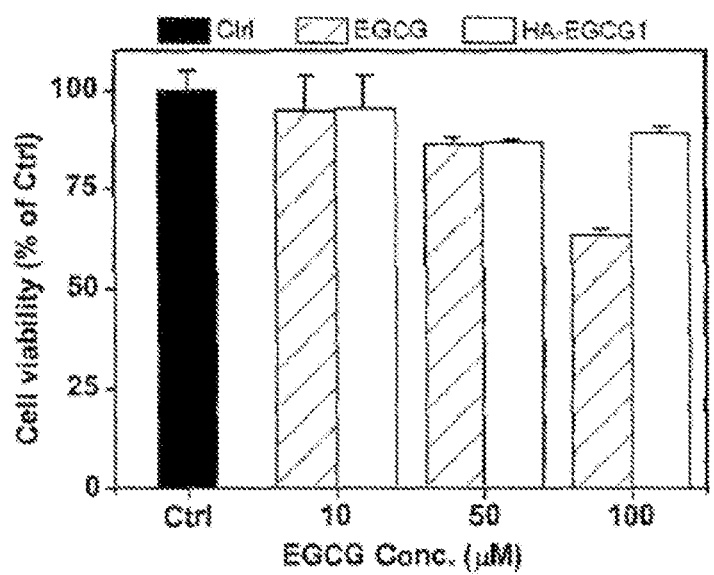
FIG. 1 shows a graph depicting the cell viability of EGCG and HA-EGCG1 conjugates using human osteoarthritis chondrocytes (HA-EGCG1 concentrations: 0.1, 0.5 and 1.1 mg/ml which contained 10, 50 and 100 μM of EGCG, respectively).
Figure 2:
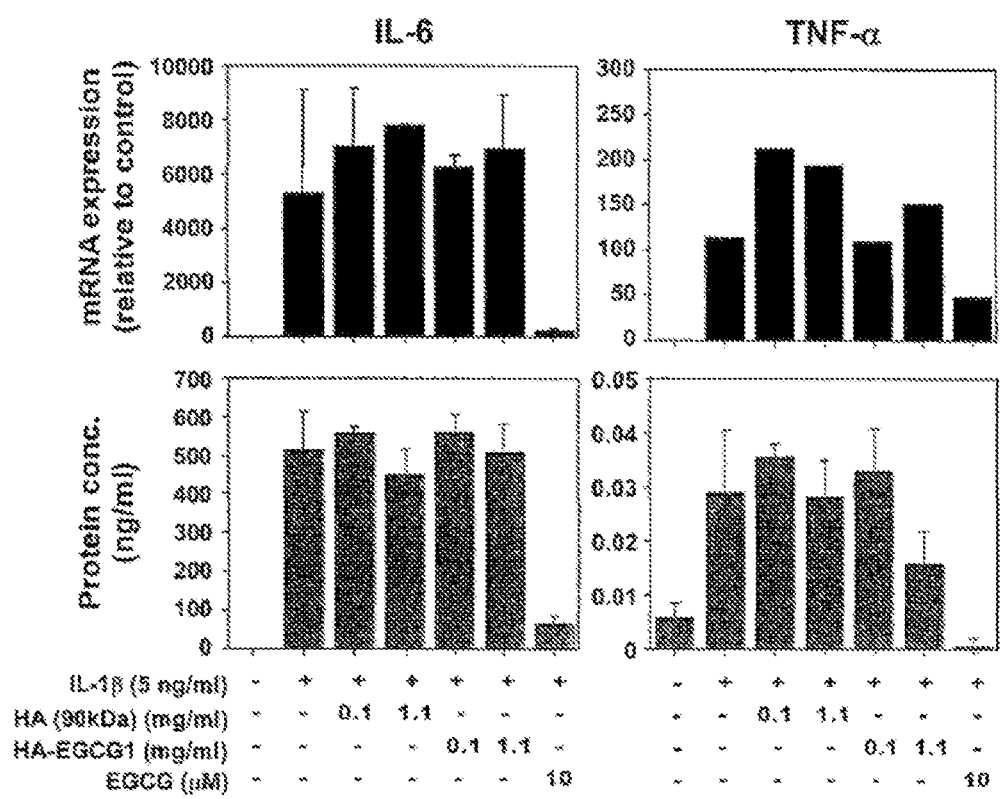

It was surprisingly found that cells were more viable in the presence of HA-EGCG1 conjugates compared to EGCG, suggesting that conjugation of EGCG to HA reduced EGCG toxicity (FIG. 1). Stimulation of osteoarthritis chondrocytes with IL-1ß increased the mRNA and protein expressions of inflammatory cytokines (FIG. 2) and MMPs (FIG. 3). While EGCG (10 μM) effectively inhibited IL-1ß-induced gene and protein expressions, HA (90 kDa) and HA-EGCG1 conjugates failed to downregulate IL-6 and TNF-u expressions (FIG. 2). However, HA-EGCG1 conjugates were surprisingly found to be more effective than HA (90 kDA) in downregulating MMP-1, MMP-3 and MMP-13 expressions, especially at the protein level (FIG. 3). Inhibition of MMP protein expressions by HA-EGCG1 conjugates were shown to be concentration-dependent. Similarly, HA-EGCG2 conjugates demonstrated lower cell toxicity compared to EGCG alone at the same EGCG concentrations (FIG. 4). HA-EGCG2 conjugates were more effective than HA (800 kDa) in downregulating IL-6, TNF-a, MMP-1, MMP-3 and MMP-13 expressions in IL-1ß-stimulated OA chondrocytes at both the gene and protein level (FIGS. 5 and 6). Increase in HA-EGCG2 concentration further reduced the gene and proteins expressions. Taken together, the results demonstrated that HA-EGCG1 and HA-EGCG2 conjugates were successful therapeutic agents for the treatment of osteoarthritis.

Example 5: Gene Expression Analysis

After serum starvation, the spent medium was removed and EGCG, HA, HA-EGCG1 or HA-EGCG2 conjugates were added in serum-free medium. After 2 h, IL-1ß (5 ng/ml) was added and the cells were incubated for another 24 h. Cells without drugs and IL-1ß stimulation served as controls. Next day, the spent medium were collected and stored in −80° C. RNA was isolated from the cells by Direct-zol™ RNA MiniPrep (Zymo Research) according to manufacturer's instructions. First strand cDNA was synthesized by RevertAid First Strand cDNA Synthesis Kit (Thermo Scientific) according to manufacturer's instructions. Real-time PCR (RT-PCR) was performed by Sensi-FAST™ Probe No-ROX Kit (Bioline) according to manufacturer's protocol using an iQ5 Real-Time PCR System (BioRad). TaqMan® Gene Expression assays were used to amplify and detect IL-6, TNF-a, MMP-1, MMP-3 and MMP-13 expressions in RT-PCR. GAPDH was used as the internal control. The threshold cycle ($C_T$) values were exported to Microsoft Excel and $\Delta\Delta C_T$ was calculated with GAPDH as the reference gene.

Example 6: Enzyme Linked Immuno-sorbant Assay (ELISA)

The concentrations of IL-6, MMP-1, MMP-3 and MMP-13 in the culture medium were determined using ELISA kits (Abeam, Hong Kong) according to the manufacturer's instructions. The concentrations of TNF-α were also determined by ELISA (Life Technologies). Preliminary experiments were performed to determine the dilution factors required for each assay to ensure that the concentration of the proteins fell within the detectable range.

Example 7: Anterior Cruciate Ligament Transection (ACLT) Model

Male Wistar rats (220-260 g) were anaesthetized with xylazine/ketamine (10/75 mg/kg) intraperitoneally. The right knee was shaved and disinfected with iodine/chlorhexidine and 70% alcohol three times alternately. After an incision was made to the skin, the joint capsule was opened. The anterior cruciate ligament (ACL) was located and severed with a pair of scissors. The skin was then closed with sutures (4-0, interrupted stitches). For the sham operation, the ACL was exposed but not transected. Baytril (10 mg/kg, SID) and buprenorphine (0.05-2 mg/kg, S.C., BID) were given for 5 and 3 days respectively after operation for prophylactic infection control and pain relief. Rats were allowed daily unrestricted cage activity after surgery and closely observed for the first 24-72 hours post-surgery.

Intra-articular (i.a.) injections were performed four weeks post-surgery. The animals were anaesthetized with isoflurane (3% induction and 2% maintenance), then 50 microliters of saline, HA (800 kDa, 10 mg/ml in saline), HA-EGCG2 conjugates (10 mg/ml in saline) were injected i.a. into the right knee. Injections were performed once a week for five consecutive weeks. Sham groups were injected with saline. Ten weeks post-surgery, the animals were euthanized by $CO_2$ and the right joints were harvested. The joints were fixed in 10% neutral buffered formalin, decalcified in 5% formic acid and subsequently embedded in parafilm. Coronal sections (7 μm) were prepared and stained with Safranin O and Fast Green. The slides were counterstained with hematoxylin. As shown in FIG. 7, although loss of proteoglycans and chondrocytes were observed in the medial tibial condyle of all treatment groups, the joints treated with HA-EGCG2 conjugates showed the presence of chondrocytes even at the edge of the cartilage (white arrows). Due to the presence of chondrocytes, it is shown that the cartilage at the knee joint is repaired.

APPLICATIONS

The disclosed polymer-flavonoid conjugates may be useful in the therapeutic and/or prophylactic treatment of a joint condition in a subject.

Advantageously, the disclosed polymer-flavonoid conjugates may be used in the treatment of osteoarthritis. The disclosed polymer-flavonoid conjugates may advantageously improve joint function and reduce pain.

Advantageously, the use of the disclosed polymer-flavonoid conjugates may potentially enhance the therapeutic outcome of the flavonoid. Further advantageously, the injection of the disclosed polymer-flavonoid conjugates of the first to third aspects may overcome the low bioavailability of flavonoids when administered orally.

There is also provided a method for making the disclosed polymer-flavonoid conjugates.

Advantageously, the disclosed method may allow for the conjugation of the polymer to the flavonoid through an efficient and cost-effective process. It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A method for treating a joint condition in a subject in need thereof comprising administering a therapeutically effective amount of a polysaccharide-flavonoid conjugate to said subject,
wherein the polysaccharide of said polysaccharide-flavonoid conjugate is conjugated to one or more flavonoids at the C2 and/or C6 position of the B ring of said flavonoid(s), and
wherein the joint condition is selected from the group consisting of osteoarthritis, rheumatoid arthritis, gouty arthritis, juvenile arthritis, psoriatic arthritis, and ankylosing spondylitis.

2. The method according to claim 1, wherein the joint condition is osteoarthritis.

3. The method according to claim 1, wherein one or more flavonoids are conjugated to said polysaccharide.

4. The method according to claim 1, wherein said polysaccharide is conjugated to said one or more flavonoids via a linker.

5. The method according to claim 1, wherein said one or more flavonoids is a monomeric flavonoid or a dimeric flavonoid.

6. The method according to claim 1, wherein the polysaccharide is conjugated to the flavonoid via a thiol linker, wherein the thiol linker further comprises a moiety bound to the polysaccharide, wherein said moiety is selected from the group consisting of an amide, an amine, an alkyl, an alkenyl, an aryl, an ester, a carbonate, an ether, an amido, an amido ester, a carbamate and an acetal group.

7. The method according to claim 1, wherein the polysaccharide is selected from the group consisting of hyaluronic acid, dextran, cellulose, amylose, starch, gelatin, alginate, chitosan, carrageenan, cyclodextrin, dextran sulfate, Ficoll, gellan, guar gum, pectin, polysucrose, pullulan, scleroglucan, xanthan and xyloglucan.

8. The method according to claim 1, wherein the flavonoid is selected from the group consisting of flavones, isoflavones, flavans, proanthocyanidins, anthocyanidins, (−)-epicatechin, (+)-epicatechin, (−)-catechin, (+)-catechin, epicatechin gallate, epigallocatechin, epigallocatechin gallate, Fisetinidol, Gallocatechin, Gallocatechin gallate, Mesquitol and Robinetinidol, ellagitannin, gallotannin, oolongtheanin, phlorotannin, tannin, theacitrin, theadibenzotropolone, theaflavin, theanaphthoquinone, thearubigins, theasinensin and mixtures thereof.

9. The method according to claim 1, the one or more flavonoids is epigallocatechin gallate and wherein the polysaccharide is conjugated to at least one epigallocatechin gallate.

10. The method according to claim 9, wherein the polysaccharide is conjugated to at least one epigallocatechin gallate via a thiol linker.

11. The method according to claim 9, wherein the polysaccharide is conjugated to at least one epigallocatechin gallate at the C2 and/or C6 ring of the B ring of said epigallocatechin gallate.

12. The method according to claim 1, wherein the polysaccharide-flavonoid conjugate is of Formula 1:

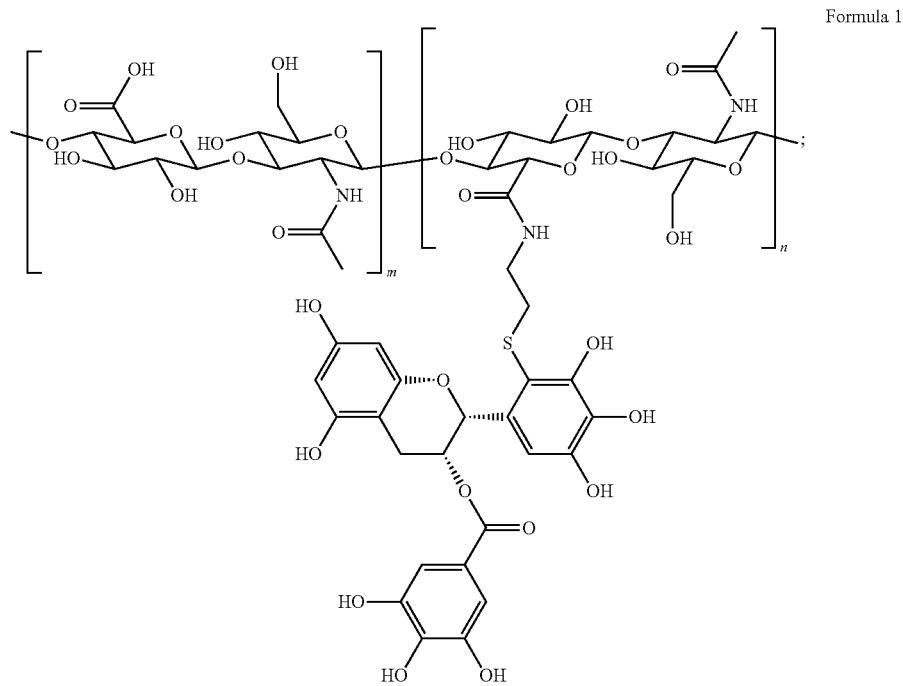

Formula 1 wherein:
each n is independently an integer from 0 to 50,000 inclusive; and each m is independently an integer from 0 to 50,000 inclusive, wherein at least one of m or n is not 0.

13. The method according to claim 12, wherein the polysaccharide-flavonoid conjugate of Formula 1 has a degree of conjugation from 0.1 to 50%.

14. The method according to claim 1, wherein said therapeutic treatment of the joint condition results in cartilage repair.

* * * * *